United States Patent [19]

Berleth et al.

[11] Patent Number: 4,690,023
[45] Date of Patent: Sep. 1, 1987

[54] CLAMPING MECHANISM FOR A CUTTER OF A MICROTOME

[75] Inventors: Manfred Berleth, Eppelheim; Helmut Weinhold, Ketsch, both of Fed. Rep. of Germany

[73] Assignee: Cambridge Instruments Inc., Buffalo, N.Y.

[21] Appl. No.: 898,742

[22] Filed: Aug. 15, 1986

Related U.S. Application Data

[63] Continuation of Ser. No. 718,251, Apr. 1, 1985, abandoned.

[30] Foreign Application Priority Data

Apr. 7, 1984 [DE] Fed. Rep. of Germany ....... 3413251

[51] Int. Cl.[4] .......................... B26D 1/02; B26D 7/26; G01N 1/06
[52] U.S. Cl. ..................................... 83/700; 83/856; 83/915.5; 83/926 H
[58] Field of Search .......... 83/915.5, 926 H, 698–700, 83/651, 856

[56] References Cited

U.S. PATENT DOCUMENTS

| 708,298 | 9/1902 | Bausch | 83/915.5 X |
|---|---|---|---|
| 1,765,283 | 6/1930 | Patterson et al. | 83/915.5 |
| 1,797,694 | 3/1931 | Ott | 83/915.5 X |
| 2,155,523 | 4/1939 | Bausch et al. | 83/416 |
| 2,232,008 | 2/1941 | MacDonald | 83/915.5 X |
| 2,662,445 | 12/1953 | Vacoby, Jr. | 83/700 |
| 3,420,130 | 1/1969 | Farquhar et al. | 83/915.5 X |
| 3,699,830 | 10/1972 | Pickett | 83/13 |
| 3,733,948 | 5/1973 | Pickett | 83/915.5 X |
| 4,472,989 | 9/1984 | Endo | 83/915.5 X |
| 4,502,358 | 3/1985 | Behme | 83/915.5 X |

FOREIGN PATENT DOCUMENTS

| 2143529 | 3/1973 | Fed. Rep. of Germany | 83/915.5 |
|---|---|---|---|
| 2415966 | 10/1974 | Fed. Rep. of Germany | 83/915.5 |

Primary Examiner—Frank T. Yost
Attorney, Agent, or Firm—Alan H. Spencer

[57] ABSTRACT

In a clamping mechanism for a blade of a microtome, in which the blade is clampable in a cutting blade mounting, the blade is supported on its front side and on its rear side in proximity with the cutting edge in the cutting region of the blade.

7 Claims, 4 Drawing Figures

CLAMPING MECHANISM FOR A CUTTER OF A MICROTOME

This application is a continuation of application Ser. No. 718,251, filed Apr. 1, 1985, now abandoned.

BACKGROUND OF THE INVENTION

The invention relates to a clamping mechanism for a cutting blade of a microtome, wherein the cutting blade is clampable in a cutting blade mounting.

Known cutting blades for microtomes are clamped, by screwthreaded bolts having two screw heads in blade holders situated on either side of the cutting edge region. In this known clamping mechanism, because the blade is clamped rigidly between two laterally spaced elements, and due to the thin section specimen held firmly in the microtome, only a relatively small cutting edge region of the expensive blade can be utilised. However, this means that the blade which is extremely costly to produce, is subject to increased wear in this narrow region, and its useful life is accordingly limited. The section removal region is further restricted by the lateral screwthreaded bolts and their screw heads.

OBJECT OF THE INVENTION

It is therefore an underlying object of the present invention to develop a clamping mechanism of the foregoing type which permits the entire cutting edge to be used.

SUMMARY OF THE INVENTION

According to the invention there is provided a clamping mechanism for clamping a cutting blade having a cutting edge and front and rear faces in a cutting blade mounting in a microtome, the clamping mechanism comprising a support for the front face of the blade and a support for the rear face of the blade in the cutting region thereof, said blade support extending into the vicinity of the cutting edge.

A particular advantage achieved by the invention is that it is possible to utilise the entire length of the cutting edge for cutting operations by sliding the cutter in the clamping mechanism. Furthermore, cutting blades with various edge geometries, and reground blades with different cutting edge angles, can be clamped securely and stably.

In one embodiment of the invention, two laterally spaced elements are connected together by a support member, and a jaw member clamping the cutting blade against the support member bridges a section removal region between the two elements and is located in the laterally spaced elements. In this way an extremely stable construction is obtained, in which any desired cutting blade, that is to say blades of any desired length or shortness, can be firmly clamped. It is even possible, in an extreme case, to clamp securely a blade that is shorter than the section removal region defined between the laterally spaced elements, and to work off such a short blade along its entire cutting edge length.

The cutting blade contact surface of the jaw member is advantageously a hollow surface and the jaw member is preferably mounted resiliently in the laterally spaced elements. By this means the jaw members, which may be in the form of a wedge, is made to abut the blade face reliably and independently of the particular wedge angle of the blade itself. In order to optimise the clearance around the jaw member, in a preferred embodiment of the invention the jaw member is slidable against a spacing piece present in each spaced element.

It is particularly advantageous if the jaw member is slidable by means of an eccentric bolt mounted in the spaced elements and arranged parallel to the cutting edge of the blade, because this results in a particularly easy to operate rapid-clamping mechanism. The ease of operation is further enhanced by the fact that only a single operating element is required to rapidly clamp or release the cutting blade in the clamping mechanism. Furthermore, the operating elements are advantageously located outside the section removal region, which permits a generously dimensioned section removal region, and makes for problem-free operation.

The cutting blade mounting is preferably pivotable about a constantly curved sliding surface formed in a base for the mounting, the axis of rotation of the mounting being coincident with the cutting edge of the blade. In this manner the angle of incidence of the blade on the particularly thin section specimen can be adjusted very simply without the need for complicated adjustment operations.

In a second embodiment of the invention a jaw member for clamping the cutting blade against a support member bridges the section removal region of the blade and the jaw member is clampable by screw means to the cutting blade and to an abutment surface of the cutting blade mounting, whilst the screw device passes between the cutting blade and the abutment surface of the mounting and is connected to the jaw member. As well as the above-described advantages, this embodiment also allows the section removal region to be dimensioned considerable more generously, due to the absence of the spaced elements projecting forwards at the sides, and the blade can be precisely and rapidly clamped in the clamping mechanism.

In order to ensure that the blade can be clamped into the clamping mechanism without any play and with great mechanical stability, the blade contact surface of the jaw member may be hollow, so that the jaw member abuts the blade by two narrow surfaces at least approximately parallel to the cutting edge, whilst the jaw member is provided with at least one further contact surface by which it abuts the abutment surface of the cutting blade mounting. Such abutment of the jaw against three distinct surface regions has the advantage of giving highly stable clamping of the blade in the clamping mechanism, even when the blade geometry deviates from a standard geometry. In a preferred embodiment of this clamping mechanism, the contact surface comprises a narrow surface at least approximately parallel to the two narrow surfaces. By providing narrow surfaces abutting the cutting blade and forming the contact surface as a narrow surface, the specific pressure between the jaw member and the clamped blade and the specific pressure between the jaw member and the abutment surface of the cutting blade mounting are relatively high, and clamping is consequently extremely stable.

The narrow surfaces and the contact surface advantageously extend across the total transverse extent of the jaw member. Constant conditions of stress are thereby produced across the total transverse extent of the clamping mechanism, so that no non-uniform wear of the clamping mechanism can occur.

In this second embodiment of the invention the screw means may comprise a screw fastened to the underside of the jaw member and secured against rotation, and a screwthreaded collar which is screwed onto the screw on the underside of the cutting blade mounting. By rotating the screwthreaded collar, the screw fastened to the jaw member is drawn against the cutter mounting, and the narrow surfaces and the contact surface of the jaw member are at the same time pressed firmly against the blade and against the abutment surface respectively, so that the blade is clamped extremely stably in the clamping mechanism.

The screwthreaded collar may be provided with a clamping lever extending out of a base for the mounting. This clamping lever is advantageously located outside the section removal region of the microtome, so that the section removal region can be generously dimensioned. This construction also gives a clamping mechanism which can be extremely easily and rapidly operated.

It is advantageous if two vertically adjustable members for supporting the cutting blade are arranged in the cutter mounting which comprises an integral support against which the cutting blade can be clamped. These adjustable members may in particular comprise fine-pitch screwthreaded bolts rotatable in the cutting blade mounting and provided with knurled nuts protruding through the mounting. These adjustable blade support members permit the cutting edge to be simply and precisely adjusted into the axis of rotation of the cutting blade mounting. In this way the cutting angle can be adjusted without difficulty, and any nonlinearities in the cutting edge of a blade can be simply compensated for.

In a preferred further development of the invention, the support member and the jaw member pressing over the area of the support member each have a wedge-shaped cross-section extending into the vicinity of the cutting edge of the blade. In this way the blade is reliably clamped virtually up to the cutting edge, and at the same time any obstruction of cutting operations is avoided.

BRIEF DESCRIPTION OF THE DRAWINGS

Further particulars, features and advantages of the invention will appear from the following description of two examples of embodiments of the invention illustrated in the accompanying drawings, in which.

DETAILED DESCRIPTION

Figure 1:
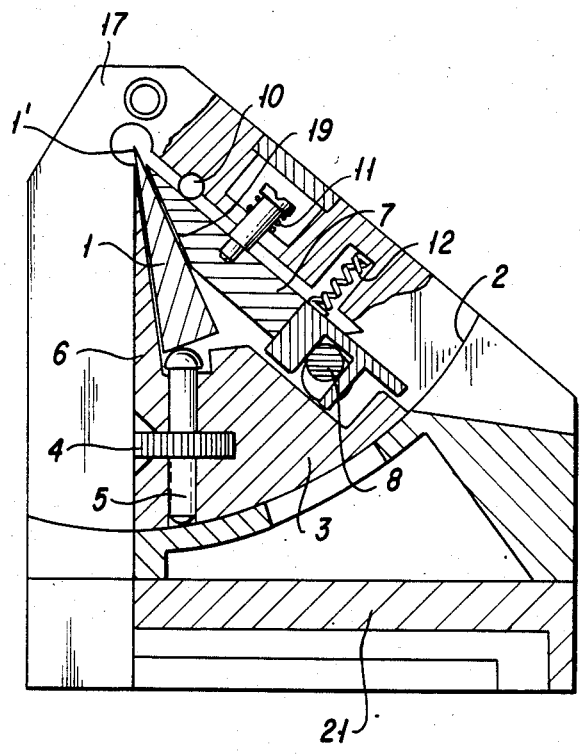
FIG. 1 shows a section through a rapid clamping mechanism.

FIG. 1 shows a cutting blade mounting 3 which contacts a base 21 over a cylrindical sliding surface 2. Cutting blade 1 is so located in the blade mounting that its cutting edge 1' lies precisely at the centre of the radius of curvature of the surface 2. It is thereby possible to adjust the cutting angle of the blade by pivoting the cutter mounting without the need to move the blade in any other way.

The precise levelling of the cutting edge 1' of the blade 1 is effected by two screwthreaded bolts 5, arranged one behind the other, upon which the blade rests, and which are vertically adjustable by means of knurled nuts 4 protruding out of the clamping mechanism.

The blade 1 is stabilised in the region of its cutting edge 1' by a wedge-shaped support member 6, which joins two laterally spaced elements 17, and which extends into the immediate vicinity of the cutting edge, but without obstructing the cutting operation.

A wedge-shaped jaw member 7 exerts a clamping force across the whole section removal region 14—14 extending between the elements 17, that is to say against the support 6. This clamping force is generated by rotating an eccentric bolt 8, mounted in the two elements, about its longitudinal axis, so that the wedge-shaped jaw 7 is driven slidably between the back of the blade 1 and a spacing piece comprising a bolt 10 located in each element 17. The blade 1 is thereby clamped. By providing a hollow front surface 19 to the jaw, a well defined linear contact may be obtained, in contrast to a relatively undefined contact surface. Compression springs 11 and 12 ensure that the jaw lies against the rear face of the blade, and can also securely abut the backs of other blades with different wedge angles.

By an appropriate rotation of the eccentric bolt 8, the jaw 7 is retracted and the blade 1 is released. It can then be slid laterally in its longitudinal direction, that is to say at right angles to the plane of the drawing, in order to bring a fresh, unused part of the cutting edge 1' into the cutting region of the microtome. The blade can then be rapidly and simply clamped once more in the clamping mechanism, as described above. If necessary, the cutting edge 1' can be re-levelled by means of the knurled nuts 4.

Figure 2:
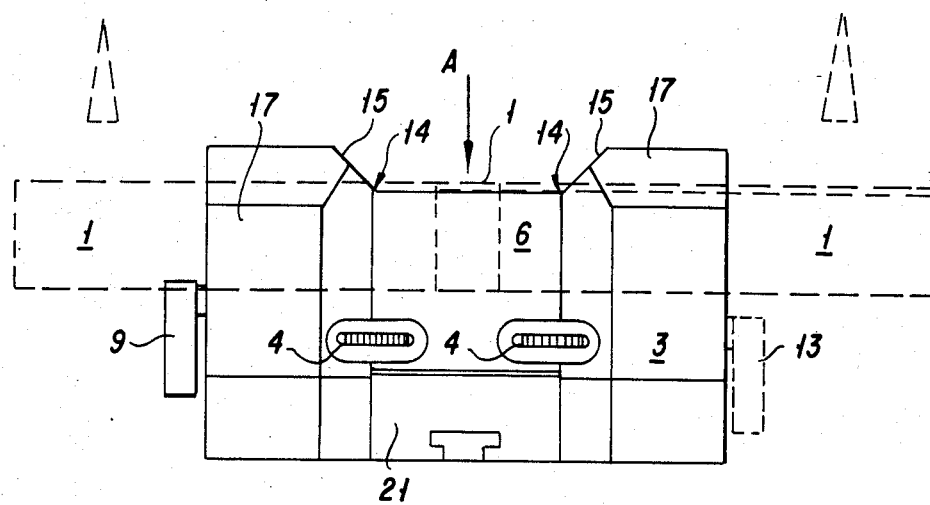
FIG. 2 shows an elevation of the clamping mechanism of FIG. 1.
Figure 3:
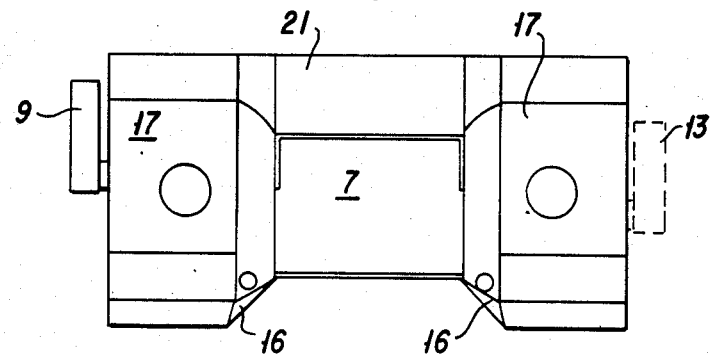
FIG. 3 shows a plan of the clamping mechanism in the direction of the arrow A in FIG. 2.

FIGS. 2 and 3 show a clamping mechanism wherein the cutting blade mounting 3 with the blade 1 clamped in it is mounted so as to be pivotable through a desired cutting angle in a base 21. The cutting angle is locked by a handle 13. As these Figures show, the blade can be clamped either in one only of the laterally spaced elements 17, or between both the lateral elements 17. In each case the blade is supported securely by the jaw 7 and by the support member 6 which connects the two elements together and which extends into the vicinity of the cutting edge 1'. Any levelling of the cutting edge which may possibly become necessary upon sliding the blade can be simply accomplished by means of the knurled nuts 4 protruding out of the cutting blade mounting 3. Rotary handle 9 serves both for clamping and releasing the blade.

As these Figures show, no control elements 9, 13 whatsoever are present in the vicinity of the section removal region 14—14; in fact, this region has been further enlarged by the use of inclined surfaces 15 and 16, to enable the clamping mechanism according to the invention to be used for problem-free section removal.

Figure 4:
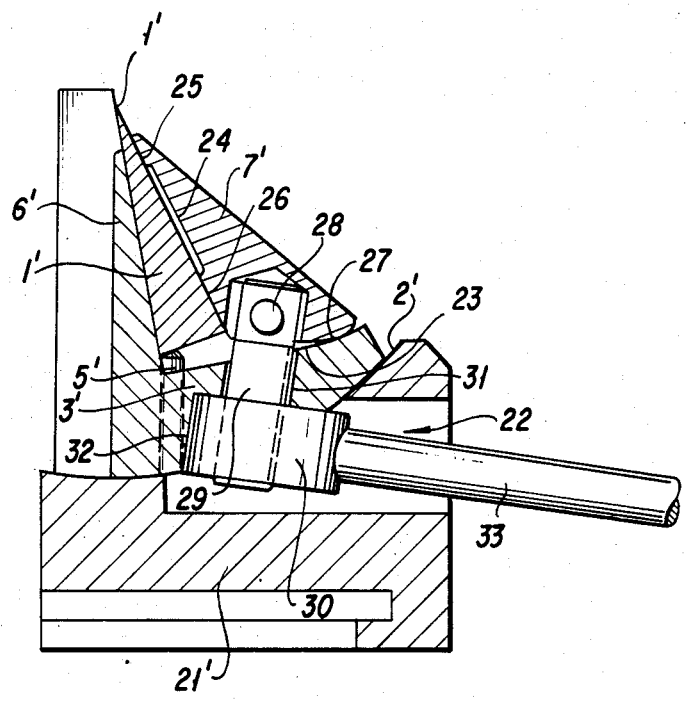
FIG. 4 shows a section through another embodiment of a rapid clamping mechanism.

FIG. 4 shows a cutting blade mounting 3' which contacts a base 21' over a cylindrical sliding surface 2'. The blade mounting and the base can be locked together in any desired position. A blade 1" is so arranged in the blade mounting that its cutting edge 1' lies precisely at the centre of the radius of curvature of the surface 2'. By pivoting the cutting blade mounting it is possible to modify the cutting angle of the blade without the need to adjust the blade in any other way.

The precise levelling of the cutting edge 1' of the blade 1" is effected by two screwthreaded bolts 5', arranged one behind the other, of which only one is indicated in this Figure, and upon which the blade 1" rests. The bolts are vertically adjustable by means of knurled nuts protruding out of the clamping mechanism.

The blade 1" is stabilised in the region of its cutting edge 1' by a wedge-shaped support member 6' which extends into the immediate vicinity of the cutting edge without obstructing cutting operations.

A jaw 7' clamping the blade 1" against the support 6' bridges the entire transverse extent of the clamping mechanism. The jaw is clampable by a screw means 22 against the blade 1" and against an abutment surface 23 of the cutting blade mounting 3'. The screw means 22 passes between the blade 1" and the abutment surface 23 of the blade mounting 3' and is rotatably connected to the jaw. The blade contact surface 24 of the jaw is a hollow surface, so that the jaw abuts the blade by two parallel narrow surfaces 25 and 26 at least approximately parallel to the cutting edge 1'. The wedge-shaped jaw has at least one further contact surface 27, by which it abuts the abutment surface 23. In order to ensure secure clamping of every blade 1" of any desired wedge-shaped cross-section, at all times, the contact surface 27 of the jaw is a narrow surface at least approximately parallel to the two narrow surfaces 25 and 26, and the narrow surfaces 25 and 26 and the contact surface 27 may extend across the total transverse extent of the jaw.

The screw means 22 comprises a screw 29 fastened to the underside of the jaw 7' between the narrow surfaces 25 and 26 and the contact surface 27 and secured against rotation by means of a pin 28, and a screwthreaded collar 30. The screw projects through a bore 31 in the cutting blade mounting 3'. The bore includes a cavity 32 which corresponds in shape to the collar 30, and against which the collar is tightened by rotation about the screw 29. By rotating the screwthreaded collar, which is provided with a clamping lever 33 extending out of the base 21' for that purpose, the jaw 7' is drawn downwards, and simultaneously its narrow surfaces 25 and 26 press against the back of the blade 1" and its contact surface 27 presses against the abutment surface 23 of the cutting blade mounting 3', is triple mounting of the jaw according to the invention produces an extremely mechanically stable and secure clamping of the cutter 1", and simultaneously permits excellent access to the cutting region of the microtome, which is accordingly extremely easy to supervise and can give problem-free operation at all times.

We claim:

1. A mechanism for clamping a rigid, wedge-shaped microtome blade having a cutting edge and opposite front and rear faces in condition for cutting wherein a cutting operation with the blade is effected by a cutting region of the cutting blade, which mechanism comprises, a base, a blade support mounted on said base defining a generally planar blade abutment face extending across said support for directly abutting the front face of the blade in the vicinity of the cutting region of the cutting blade, a jaw including means defining two narrow blade-engaging surfaces extending transversely of and across the total transverse extent of the jaw and arranged relative to said blade support so that each of said narrow blade-engaging surfaces directly opposes said blade abutment face along the entire length of said blade-engaging surfaces, said jaw being movably mounted on said support for movement relative to said blade abutment face between one jaw position at which a blade which has been operatively positioned within said mechanism so that the front face therof operatively abuts said blade abutment face is stably secured between said jaw and said blade abutment face in the vicinity of the cutting region of the blade as said two narrow blade-engaging surfaces of the jaw and only said two narrow blade-engaging surfaces engage the back face of the blade and effectively press the blade against said blade abutment face and another jaw position at which said two narrow blade-engaging surfaces are in condition for releasing the blade from the mechanism, and means acting between said blade support and said jaw for releasably urging said jaw from said another jaw position to said one jaw position so that when a rigid, wedge-shaped blade is operatively positioned between said blade abutment face and said jaw and said jaw is said urged by said urging means from said another jaw position to said one jaw position, the blade is securely clamped in the vicinity of the cutting region of the cutting blade used for cutting and so that movement of said jaw from said one position to said another position permits the blade to be shifted relative to and across said support for operatively positioning an alternative cutting region of the cutting blade between said jaw and said abutment face thereby permitting substantially all of the blade to be used.

2. The mechanism of claim 1, wherein said jaw has a hollow-ground surface defined between said two narrow blade-engaging surfaces.

3. The mechanism of claim 1, wherein said jaw has a recess defined between said two narrow blade-engaging surfaces.

4. The mechanism of claim 1, wherein said support tapers toward a top edge, a pair of elements, one of said pair being attached to one end of said support and the other of said pair being attached to the other end of said support, each of said pair having a wedge-shaped passage having an apex, each passage being adapted to receive a portion of said jaw extending beyond the cutting region.

5. The mechanism of claim 4 wherein an eccentric urges said jaw toward the apex of said passage.

6. A clamping mechanism according to Claim 1, wherein said support is pivotable on a constantly curved sliding surface formed in said base, the axis of rotation of the mounting being coincident with the cutting edge of the blade.

7. A clamping mechanism according to cClaim 1, wherein said jaw is releasably urged toward said abutment face by a screw cooperating between said support and said jaw.

* * * * *